United States Patent [19]

Knifton et al.

[11] Patent Number: 5,387,722
[45] Date of Patent: Feb. 7, 1995

[54] ONE-STEP SYNTHESIS OF METHYL T-BUTYL ETHER FROM T-BUTANOL USING PENTASIL ZEOLITE CATALYSTS

[75] Inventors: John F. Knifton, Austin; Pei-Shing E. Dai, Port Arthur, both of Tex.

[73] Assignee: Texaco Chemical Inc., White Plains, N.Y.

[21] Appl. No.: 125,271

[22] Filed: Sep. 23, 1993

[51] Int. Cl.$^6$ ............................................. C07C 41/09
[52] U.S. Cl. ................................................... 568/698
[58] Field of Search ..................................... 568/698

[56] References Cited

U.S. PATENT DOCUMENTS 4,886,918  12/1989  Sorensen et al. ............... 568/698
5,162,592  11/1992  Knifton et al. .................. 568/698
5,243,091   9/1993  Kruse et al. ..................... 568/698

*Primary Examiner*—Howard T. Mars
*Attorney, Agent, or Firm*—James L. Bailey; Kenneth R. Priem; Cynthia L. Hunter

[57] ABSTRACT

Disclosed is a process for preparing alkyl tertiary alkyl ethers in one step which comprises reacting tert-butanol and a $C_1$–$C_4$ primary alcohol in the presence of a catalyst consisting essentially of a pentasil zeolite having a silica/alumina ratio of 50–150, optionally with a binder at a temperature of about 80° to 200° C. and atmospheric pressure to about 1000 psig, wherein when the temperature is in the operating range above 140° C., the product comprises a two-phase mix of a MTBE or ETBE and isobutylene product-rich phase and a heavier aqueous primary alcohol-rich phase.

8 Claims, No Drawings

ONE-STEP SYNTHESIS OF METHYL T-BUTYL ETHER FROM T-BUTANOL USING PENTASIL ZEOLITE CATALYSTS

CROSS-REFERENCE

This application is related to pending U.S. Ser. No. 07/967,479 and 08/057,373. It is also related to U.S. Pat. Nos. 4,822,921; 4,827,048; 5,099,072; 5,081,318; 5,059,725; 5,157,162; 5,162,592; 5,157,161; 5,183,947; and allowed U.S. Ser. Nos. 07/917,218; 07/878,121; and 07/917,885, all of which are incorporated by reference herein in their entirety.

1. Field of the Invention

This invention concerns an improved process for preparing methyl tertiary butyl ether (MTBE) or ethyl tertiary butyl ether (ETBE) in one step by the reaction of tertiary butanol and ethanol in the presence of a catalyst comprising a pentasil zeolite, specifically one having a Si/Al ratio in the range 31–350 and preferably a Si/Al ratio in the range 50–150, optionally with a binder from Group III or IV of the Periodic Table. The invention is especially advantageous in that the pentasil zeolites exhibit high activity during methyl t-butyl ether synthesis from methanol and t-butanol or ethyl t-butyl ether synthesis from ethanol plus t-butanol and, additionally, allow for the cosynthesis of isobutylene and diisobutylene.

2. Background of the Invention

It is well-known that there is pressure to eliminate lead compounds from fuels for reasons of public health and environmental protection. Although the specifications for reformulated gasolines set by EPA will come into force in 1995, standards were brought into force on Nov. 1, 1992 requiring gasoline contain 2.7 wt % oxygen during the winter in nonattainment areas of the U.S. If the federal air quality standard for CO has not been achieved by a specified attainment date, the minimum oxygen content will increase to 3.1%. Moreover, starting in the summer of 1992, the maximum blending Reid vapor pressure (BRvp) of all gasolines is set at 9.0 psi. Since oxygenates are not only used as gasoline blending components, extenders, octane boosters and as key ingredients for reducing the emissions of CO and VOCs (Volatile Organic Compounds), it is expected that the demand for oxygenates will increase enormously in the coming years. See F. Cunill, et al., "Effect of Water Presence on Methyl tert-Butyl Ether and Ethyl tert-Butyl Ether Liquid-Phase Synthesis". *IND. ENG. CHEM. RES.* 1993, 32, 564–569.

Of all oxygenates, the tertiary ethers, such as methyl t-butyl ether (MTBE), ethyl tert-butyl ether (ETBE), and tert-amyl methyl ether (TAME) are preferred by refineries to lighter alcohols. They have lower blending Ried vapour pressure (BRvp), lower vaporization latent heats and low solubilities in water. The most common ether in use today is MTBE with a production of about 25 million metric tons. However, ETBE is becoming more attractive as the price of methanol goes up in relation to gasoline. It can be produced from renewable ethanol, in contrast to methanol derived from natural gas, and its use would help mitigate the greenhouse effect, Ibid., p. 564.

In addition, ETBE outranks MTBE as an octane enhancer and its BRvp is only 4 psi, which makes it more attractive for BRvp blends less than 8 psi required in some places during the summer. Therefore, a number of U.S. states and European countries are planning to make ETBE from bioethanol, Ibid.

At the present time, TAME, which is usually produced in MTBE refinery units when $C_5$ olefins are diverted into the feed, is not viewed as rivaling MTBE or ETBE, Ibid.

The main drawback of tertiary ethers, is that they substantially increase aldehyde emissions which are under EPA regulations and have to decrease 15% by 1995. It is believed this drawback could be largely circumvented by mixing the tertiary ethers with tertiary alcohols. Tertiary butyl alcohol (tBA) has a very low atmospheric reactivity and low aldehyde emissions, since no hydrogens are contained in the carbon link to the oxygen. Basis experience acquired with tBA during the 1970s, a gasoline blended with a mixture of ethers and tBA and/or tertiary amyl alcohol should be shippable, Ibid.

It is known in the art to produce ETBE or MTBE by reacting isobutylene with either ethanol or methanol, resulting in the formation of ETBE or MTBE, respectively. The reaction normally is conducted in liquid phase with relatively mild conditions. The isobutylene can be obtained from various sources, such as naphtha cracking, catalytic cracking, etc. The resulting reaction product stream contains the desired MTBE or ETBE, as well as unreacted isobutene and other $C_4$ hydrocarbons and methanol or ethanol.

A number of U.S. patents, and allowed U.S. applications, assigned to Texaco Chemical Co. disclose methods of making alkyl tertiary alkyl ethers, including MTBE and ETBE, in one step, from tert-butanol rather than isobutylene.

In U.S. Pat. No. 4,822,921, to Texaco Chemical Co., there is described a method for preparing alkyl tertiary alkyl ethers which comprises reacting a $C_1$–$C_6$ primary alcohol with a $C_4$–$C_{10}$ tertiary alcohol over a catalyst comprising an inert support impregnated with phosphoric acid.

U.S. Pat. No. 4,827,048, to Texaco Chemical Co., describes a method for preparing alkyl tertiary alkyl ethers from the same reactants using a heteropoly acid on an inert support.

U.S. Pat. No. 5,099,072, to Texaco Chemical Co., discloses a method for preparing alkyl tertiary alkyl ethers over an acidic montmorillonite clay catalyst which possesses very specific physical parameters.

U.S. Pat. No. 5,081,318, to Texaco Chemical Co., discloses a method for preparing alkyl tertiary alkyl ethers by reacting a $C_1$–$C_6$ primary alcohol with a $C_4$–$C_{10}$ tertiary alcohol over a catalyst comprising a fluorosulfonic acid-modified zeolite.

U.S. Pat. No. 5,059,725, to Texaco Chemical Co., discloses a method for preparing alkyl tertiary alkyl ether from $C_1$–$C_6$ primary alcohols and $C_4$–$C_{10}$ tertiary alcohols over a catalyst comprising ammonium sulfate or sulfuric acid on a Group IV oxide.

U.S. Pat. No. 5,157,162, to Texaco Chemical Co., discloses a fluorosulfonic acid-modified clay catalyst for the production of alkyl tertiary alkyl ethers from $C_1$–$C_6$ primary alcohols and $C_4$–$C_{10}$ tertiary alcohols.

In U.S. Pat. No. 5,162,592, to Texaco Chemical Co. there is described a method for producing alkyl tertiary alkyl ethers from $C_1$–$C_6$ primary alcohols and $C_4$–$C_{10}$ tertiary alcohols using a multimetal-modified catalyst.

A hydrogen fluoride-modified montmorillonite clay catalyst is employed in U.S. Pat. No. 5,157,161, to Texaco Chemical Co., to produce alkyl tertiary alkyl ethers.

In U.S. Pat. No. 5,183,947, to Texaco Chemical Co., fluorophosphoric acid-modified clays are employed as catalysts in a method to produce alkyl tertiary alkyl ethers.

In allowed U.S. Serial No. 07/917,218, assigned to Texaco Chemical Co., there is disclosed the use of a super acid alumina or a faujasite-type zeolite to produce alkyl tertiary alkyl ethers.

Allowed U.S. Ser. No. 07/878,121, to Texaco Chemical Co., discloses the use of a haloacid-modified montmorillonite clay catalyst to convert $C_1$–$C_6$ primary alcohols and $C_4$–$C_{10}$ tertiary alcohols to alkyl tertiary alkyl ethers.

Fluorophosphoric acid-modified zeolites are employed in allowed U.S. Ser. No. 07/917,885, to Texaco Chemical Co., to produce alkyl tertiary alkyl ethers.

Other references in the art which disclose MTBE and ETBE as products usually require two stages rather than one and use isobutylene as a reactant.

For example, in U.S. Pat. No. 4,334,890, a mixed $C_4$ stream containing isobutylene is reacted with aqueous ethanol to form a mixture of ethyl tertiary butyl ether (ETBE) and tertiary butyl alcohol (tBA). U.S. Pat. No. 5,015,783 describes a process for producing ethers, including ETBE which comprises passing a feed stream to an etherification zone, passing the etherification zone effluent stream to a distillation column and further involves cooling the overhead stream, refluxing and recycling.

A process for the production of ETBE and/or MTBE is disclosed in U.S. Pat. No. 2,480,940.

U.S. Patents which discuss the production of ETBE as well as MTBE include:
5,070,016
4,440,063
4,962,239
4,015,783

These patents all use isobutylene as the coreactant rather than t-butanol.

Pentasil Zeolites

The characteristic structures of catalytically important molecular sieve zeolites are discussed in "Molecular Sieve Catalysts," by J. Ward, Applied Industrial Catalysis, Vol. 3, Ch. 9, p. 271 (1984). Molecular sieve zeolites which have been investigated in most detail are those which have achieved industrial application, namely, X, Y, mordenite, the pentasil types and erionite.

The pentasil family of zeolites contains a continuing series of which ZSM-5 and ZSM-11 are end members. See T. E. Whyte et al. "Zeolite Advances in the Chemical and Fuel Industries: A Technical Perspective," CATAL. REV.-SCI ENG., 24,(4), 567–598 (1982).

The article by J. W. Ward, supra, presents an excellent review of pentasil type zeolites. The pentasils usually have a Si/Al ratio greater than 10. A more detailed description of pentasil zeolites follows under the "Description of the Catalyst."

A good overview of applications for zeolites, including pentasil type zeolites is found in an article titled, "Zeolite Catalysts Face Strong Industrial Future", European Chemical News Jul. 10, 1989, p. 23. For example, medium pore H-ZSM-5 is sometimes added to a zeolite Y catalytic cracking catalyst to increase the aromatics content and hence motor octane, of the gasoline fraction. In the limited space of ZSM-5, where two pore systems of about 5–6 Å in diameter intersect to give spatial regions of around 9 Å diameter at the intersections, there is a cutoff around $C_{10}$ to $C_{11}$ for products from transformation of a wide range of feedstocks, including alkanes, olefins and alcohols.

ZSM-5 is a catalyst used for converting methanol to gasoline, processing C-8 streams, selectively isomerizing m-cresol to p-cresol, suppressing the formation of diphenylalanine in the production of aniline, and producing pyridine and $\beta$-picoline from acetaldehyde, formaldehyde and ammonia.

In an Article titled "Shape Selective Reactions with Zeolite Catalysts", *J. CATAL.*, 76, 418 (1982), L. B. Young et al. report data on selectivity in xylene isomerization, toluene-methanol alkylation, and toluene disproportionation over ZSM-5 zeolite catalysts. Some of the ZSM-5 zeolites in this study were modified. It was demonstrated that appropriately modified ZSM-5 class zeolites are capable of generating uniquely selective compositions. Intrinsic reactivities and selectivities are considerably altered with these modified catalysts.

There is a discussion of the shape selective properties of ZSM-5 in "A Novel Effect of Shape Selectivity: Molecular Traffic Control In Zeolite ZSM-5", by E. G. Derouane, et al., *J. CATAL.*, 65, 486 (1980). Some of the observations included the following: (i) linear aliphatics diffuse rather freely in the ZSM-5 framework and can be adsorbed in both channel systems; (ii) isoaliphatic compounds experience steric hinderance which may restrict their diffusion in the sinusoidal channel system; and (iii) aromatic compounds and methyl substituted aliphatics have a strong preference for diffusion and/or adsorption in the linear and elliptical channels.

E. G. Derouane et al. studied shape selective effects in the conversion of methanol to higher hydrocarbons and alkylation of p-xylene on pentasil-family zeolites. Some of these zeolites were modified by the incorporation of phosphorous, or embedded in a silica filler. Their findings are reported in "Molecular Shape Selectivity of ZSM-5, Modified ZSM-5 and ZSM-11 Type Zeolites", in *FARADAY DISCUSSIONS*, 72, 331 (1981).

It has been reported in the art that methyl t-butyl ether could be prepared from isobutylene over zeolite catalysts.

P. Chu et al. report results of one study in "Preparation of Methyl tert-Butyl Ether (MTBE) over Zeolite Catalysts", *IND. ENG. CHEM. RES.*, 26, 365 (1987). They reported that ZSM-5 and ZSM-11 have been identified to be highly selective zeolite catalysts for the preparation of MTBE from isobutylene. Compared to the conventional commercial catalyst, Amberlyst 15 resin, the pentasil zeolites are thermally stable, give no acid effluent and are less sensitive to the methanol-to-isobutene ratio. The excellent selectivity is believed to be effected by the size of their pore structure, which provides easy access to methanol and restricted access to isobutene. In contrast, small pore zeolites such as synthetic ferrierite were found inactive. Large pore zeolites, such as high-silica mordenite and zeolite Beta were not expected to exhibit shape selectivity.

Another reference which discusses the use of pentasil zeolites in MTBE service is by G. H. Hutchings, et al., *CATAL. TODAY*, 15, 23 (1992).

It would represent a distinct advance in the art if tertiary butanol, instead of isobutylene, could be converted to methyl tertiary butyl ether or ethyl tertiary butyl ether over a catalyst which exhibited extended life and good conversions at moderate temperatures.

The available art does not appear to teach the use of a pentasil type zeolite for synthesis of MTBE or ETBE using t-butanol. Neither does it suggest the possibility of phase separation at temperatures greater than 160° C., nor the cosynthesis of isobutylene along with MTBE and ETBE.

SUMMARY OF THE INVENTION

In accordance with certain of its aspects, the novel method of this invention for preparing methyl tertiary butyl ether (MTBE) or ethyl tert-butyl ether (ETBE) from tertiary butyl alcohol and methanol or ethanol in one-step comprises reacting tertiary butyl alcohol and methanol or ethanol in the presence of a catalyst comprising pentasil zeolite having a silica-to-alumina ratio in the range 30–350, optionally with a binder from Group III or IV of the Periodic Table, at an elevated temperature and moderate pressure.

Typically effluent concentrations of about 41% and 28%, respectively, have been achieved and tertiary butanol conversion levels of 68% and 59% at 120° C., respectively. The highest etherification activity is realized at 120° C.

DESCRIPTION OF THE INVENTION

Preparation of the product of this invention may be carried out typically by reacting tertiary butyl alcohol and methanol or ethanol in the presence of a pentasil zeolite with a binder. The etherification is carried out in one-step and the catalyst preferably comprises a pentasil zeolite having a silica/alumina ratio in the range of 30–350, and preferably 50–150 with 1% to 40% Group III or IV binder.

The reaction can be represented by the following:

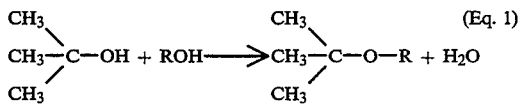

(Eq. 1)

Generally the methanol or ethanol and t-butanol coreactants may be mixed in any proportion in order to generate the desired methyl tertiary butyl ether (MTBE) or ethyl t-butyl ether (ETBE), but preferably the molar ratio of alkanol to t-butanol (tBA) in the feed mixture should be between 10:1 and 1:10, if the yield of desired ether is to be maximized. In order to achieve maximum selectivity to MTBE or ETBE, and optimum conversion per pass, an excess of methanol or ethanol in the liquid feed is desirable. The most preferred alkanol-to-tertiary butanol molar ratio is from 1:1 to 5:1.

In certain circumstances, it may be particularly desirable that the tBA conversion be high enough (e.g. 60% or greater), such that the crude product mix phase separates into an isobutylene-MTBE/ETBE product-rich phase and a heavier aqueous ethanol or methanol phase. The phase containing MTBE or ETBE and isobutylene contains essentially no diisobutylene. Preferably such a product phase separation would be achieved at as low an etherification temperature as possible, but it is particularly observed in the range 160° –200° C.

The synthesis of Eq. 1 can also be conducted where the t-butanol and methanol or ethanol reactants are mixed certain other components including water, ketones such as acetone ($Ac_2O$) and methyl ethyl ketone (MEK), peroxides and hydroperoxides such as di-t-butyl peroxide (DTBP), allyl t-butyl peroxide (ATBP), and t-butyl hydroperoxide (TBHP), as well as esters such as t-butyl formate (TBF). Typically each of said classes of components makes up less than 10% of the total feed mixture.

The instant one-step process may also be applied to the preparation of other alkyl tertiary alkyl ethers. For example, said process may be applied to the reaction of a $C_1$–$C_6$ primary alcohol (ROH in Eq. 1) such as methanol, ethanol, n-propanol and n-hexanol with a $C_4$–$C_{10}$ tertiary alcohol such as, for example, tertiary butanol and tertiary amyl alcohol. Reaction of methanol with t-butanol would yield methyl tert-butyl ether (MTBE), while reaction of methanol with tertiary amyl alcohol (2-methyl-2-butanol) would then yield methyl tertiary amyl ether (TAME). Alternatively a mixture of alcohols, e.g., a mixture of $C_1$–$C_5$ alcohols, could be reacted to give a mixture of alkyl tert-alkyl ethers.

In the modified catalyst of the instant invention good results were realized using certain crystalline aluminosilicate zeolites, optionally with a binder, as catalysts for the reaction represented in Eq. 1. Particularly effective were the isostructural group of pentasil zeolites.

As mentioned, Ward, Supra, p. 271 provides an overview of the structure of pentasils. These zeolites, as well as silicalite have $SiO_2$—$Al_2O$ ratios greater than 10. Silicalicate, ZSM-5, ZSM-11 and related materials have structures with ten-ring channel systems in contrast with the eight-membered zeolites such as A and erionite and the twelve-membered systems such as zeolites X and Y.

Pentasil zeolites are hydrophobic compared with A, X and Y zeolites. ZSM-5 has orthorhombic unit cells, whereas ZSM-11 is tetragonal.

The pentasil structures are very thermal and acid stable. They are synthesized in the presence of ammonium ions, which become an integral part of the structure. Heating up to 600° C. decomposes the organic cations leaving the highly porous structure.

The channel size of pentasil materials is intermediate between, for example, small pore erionite and large pore zeolite Y. Hydrocarbons such as o- and m-xylene, 1,2,4-trimethylbenzene and naphthalene, with minimum diameters of about 6.9 Å are absorbed slowly whereas 1,3,5-trimethylbenzene is excluded. Benzene and p-xylene diffuse readily in ZSM-5 whereas larger molecules such as o-xylene diffuse slowly. Highly branched paraffins diffuse much more slowly than normal and monobranched.

Other ZSM series zeolites are not considered to be pentasils. ZSM-21, ZSM-35 and ZSM-38 are considered to be of the ferrierite type zeolite. ZSM-20 is considered of the faujasite type and ZSM-34 is considered to be of the offretite/erionite group. Whyte, supra, p. 571.

Medium pore, pentasil-type zeolites having 10-membered oxygen ring systems include, for example, ZSM-5, ZSM-11, ZSM-22, ZSM-23, ZSM-48 and laumontite. Their framework structures contain 5-membered oxygen rings and they are more siliceous than previously known zeolites. In many instances these zeolites may be synthesized with a predominance of silicon and with only a very small concentration of other atoms such as aluminum; thus, these zeolites may be considered as "silicates" with framework substitution by small quantities of other elements such as aluminum. Among the zeolites in this group, only ZSM-5 and ZSM-11 have bidirectional intersecting channels, the others have nonintersecting unidirectional channels.

The medium-pore pentasils, unlike other zeolites, have pores of uniform dimension and have no large supercages with smaller size windows. This particular feature is believed to account for their unusually low coke-forming propensity in acid-catalyzed reactions. Because the pentasil zeolites are devoid of the bottlenecks in the window/cage structure, molecules larger than the size of the channel do not form with the exception perhaps at the intersections.

The preferred forms of pentasil zeolite are the highly acidic, high silica forms, having silica-to-alumina mole ratio of at least 30:1, and preferably in the range of 30:1 to 350:1 in the as-synthesized form. A narrower range of 50:1 to 150:1 is preferred and the pentasil zeolites demonstrated in the examples possess $Si_2/Al_2O_3$ ratios of about 31:1 to ca. 350:1.

Generally, it can be said that changes in the Si/Al ratio from one to infinity result in predictable changes in:

Stability, from <700° C. to ~1300° C.
Surface selectivity, from hydrophilic to hydrophobic
Acidity increasing in intrinsic strength
Cation concentration decreasing
Structure from 4-, 6- and 8-rings to 5-rings.

See "Industrial Catalytic Applications of Molecular Sieves" by P. R. Pujadó, et al. in CATAL. TODAY, 13, 113–141 (1992).

The thermal stability of the crystalline lattice of zeolites varies substantially, from about 700° C. for aluminum-rich zeolites, to about 1300° C. for silicalite. Aluminum-rich zeolites are unstable in the presence of acids, while silicon-rich zeolites are stable even in concentrated mineral acids. In contrast, silicon-rich zeolites exhibit low stability in basic solutions. Likewise, aluminum-rich zeolites exhibit a highly-polar hydrophilic surface. Silicon-rich zeolites tend to be more nonpolar and hydrophobic. The onset of hydrophobicity appears to occur at a Si/Al ratio of about 10.

The silica-to-alumina ratios referred to in this specification are the structural or framework ratios, that is, the ratio of the $SiO_4$ to the $AlO_4$ tetrahedra, which together constitute the structure of which the zeolite is composed. It should be understood that this ratio may vary from the silica-to-alumina ratio determined by various physical and chemical methods. For example, a gross chemical analysis may include aluminum which is present in the form of cations associated with the acidic sites on the zeolite, thereby giving a low silica-to-alumina ratio. Similarly, if the ratio is determined by the thermogravimetric analysis (TGA) of ammonia desorption, a low ammonia titration may be obtained if cationic aluminum prevents exchange of the ammonium ions onto the acidic sites. These disparities are particularly troublesome when certain treatments, such as dealuminization, which result in the presence of ionic aluminum free of the zeolite structure, are employed. Due care should therefore be taken to ensure that the framework silica-to-alumina ratio is correctly determined.

The silica-to-alumina ratio of the zeolite may be determined by the nature of the starting materials used in its preparation and their quantities relative one to another. Some variation in the ratio may therefore be obtained by changing the relative concentration of the silica precursor relative to the alumina precursor, but definite limits in the maximum obtainable silica-to-alumina ratio of the zeolite need be observed. For a pentasil zeolite, this limit is usually about 350:1 (although higher ratios may be obtained) and for ratios above this value, other methods are usually necessary for preparing the desired high silica zeolite. This method generally comprises contacting the zeolite with an acid, preferably a mineral acid such as hydrochloric acid.

Example 1 demonstrates the use of ZSM-5. ZSM-5 can be synthesized by including organic molecules such as tetrapropylammonium bromide in the reaction mixtures. The organic molecules are incorporated into the zeolite crystal interstices as the zeolite is formed. See R. J. Argauer et al., U.S. Pat. No. 3,702,886 (Nov. 14, 1972); L. D. Rollmann, Inorganic Compounds with Unusual Properties, Vol. 2 (R. B. King, ed.), Am. Chem. Soc., New York, 1979, p. 387; D. H. Olson, W. O. Haag, and R. M. Lago, J. CATAL., 61, 390 (1980); G. T. Kerr, CATAL. REV.-SCI. ENG.,23, 281 (1981).

Properties of ZSM-5 which are of significance to shape-selective catalysis are the presence of two intersecting channels formed by rings of 10 oxygen atoms. The two intersecting channels, both formed by 10-membered oxygen rings, are slightly different in their pore size. One runs parallel to the a-axis of the unit cell; it is sinusoidal and has a nearly circular (5.4×5.6 Å) opening. The other runs parallel to the b-axis and has a straight, but elliptical opening (5.1×5.5 Å). See W. M. Meier and D. H. Olson, Atlas of Zeolite Structure Types, International Zeolite Assoc., Polycrystal Book Service, Pittsburgh, 1978.

The instant catalysts may be formed in the presence of a binder, such as Group III or Group IV oxide, including alumina or silica. Said binders may comprise 1% to 40% of the formed catalyst.

The zeolites are combined with a binder by a variety of forming techniques. Said catalysts may be in the form of powders, pellets, granules, spheres, shapes and extrudates. The examples described herein demonstrate the advantages of using extrudates.

The reaction may be carried out in either a stirred slurry reactor or in a fixed bed continuous flow reactor. The catalyst concentration should be sufficient to provide the desired catalytic effect.

Etherification can generally be conducted at temperatures from 20° to 250° C.; the preferred range is 80° to 200° C. Good results are observed throughout this temperature range. However, it can be noted that the best tBA conversion figures are observed when the temperature is around 140° C. or higher. The total operating pressure may be from 0 to 1000 psig, or higher. The preferred pressure range is 50 to 500 psig.

Typically, MTBE or ETBE is generated continuously in up to ca. 40 wt % concentration or greater in the crude liquid product at total liquid hourly space velocities (LHSV) of up to 6 or higher and relatively mild conditions, where:

$$LHSV = \frac{\text{Volume Of Total Liquid Feed Run Through The Reactor Per Hour}}{\text{Volume of Catalyst In Reactor}}$$

Conversions of t-butanol (tBA, wt %) are estimated in the following examples using the equation:

$$\frac{(\text{Mole \% of } tBA \text{ in Feed} - \text{Mole \% of } tBA \text{ in Product})}{\text{Mole \% of } tBA \text{ in Feed}} \times 100$$

The examples which follow illustrate the one-step synthesis of MTBE or ETBE from tBA and MeOH or EtOH (Eq. 1) using pentasil zeolites having a silica/alumina ratio of ca. 30–350, optionally with a binder, particularly in the form of extrudates.

The accompanying examples illustrate:

1) The cosynthesis of MTBE plus isobutylene from t-butanol plus methanol using a series of pentasil, ZSM-5 type catalysts with different silica/alumina ratios (see Examples 1–4, Tables 1–4). Here the highest t-butanol conversion levels at 120° C. are realized with the ZSM-5 catalyst having silica/alumina ratios of 50→140. Product phase separation is observed at 160° C. for a number of these ZSM-5 catalysts.

2) In Example 5, the cosynthesis of ETBE and isobutylene from tBA/ethanol is illustrated using ZSM-5 where the conversion levels for tBA are 59% at 120° C. and 84% at 160° C. (see also Table 5).

3) In Example 6, the cosynthesis of ETBE and isobutylene from tBA/ethanol is illustrated using a crude feedstock also containing sizeable quantities of water, isopropanol, acetone and methyl ethyl ketone. An extended catalyst life study with this feed has been demonstrated (see Table 6), where t-butanol conversion levels remain in the region of ca. 50% per pass and there is essentially no by-product diisobutylene ($C_8H_{16}$) or diethyl ether (DEE) formation.

EXAMPLE 1

This example illustrates the production of methyl t-butyl ether from t-butanol and methanol using a pentasil-type zeolite.

Synthesis was conducted in a tubular reactor ($\frac{3}{8}$" i.d., 12" long) constructed of 316 stainless steel, operated upflow, and mounted in a furnace, controllable to ±1.0° C. and fitted with pumps allowing flow control to <±1 cc/hr). The reactor was also fitted with a pressure regulating device and equipment for monitoring temperature, pressure and flow rate.

The reactor was charged at the beginning of the experiment with 25 cc of ZSM-5 zeolite having a silica/alumina ratio of 140, with 20% alumina binder, as 1/16" diameter extrudates. A glass wool screen was placed at the top and bottom of the reactor to ensure the catalyst would remain in the middle portion.

The catalyst bed was treated with methanol/t-butanol (1.1:1 molar mix) upflow, at a rate of 50 cc/hr, while the reactor was held at 120° C., with a total pressure of 300 psi. Samples of crude product effluent were collected periodically on-stream, in 316 ss bombs and analyzed by glc.

Typical analyses data for samples taken under these conditions are summarized in Table 1. Concentrations of MTBE, isobutylene ($C_4H_8$), diisobutylene ($C_8H_{16}$), alkyl ether (DME), and t-butanol (tBA) in the reaction effluent were also measured at a series of higher temperatures (140°–160° C.). These data are also included in Table 1.

| For Sample #1, at 120° C.: | |
|---|---|
| tBA Conversion = | 68% |
| MTBE Selectivity = | 75% |
| Isobutylene Selectivity = | 24% |
| For Sample #5, at 160° C.: | |
| tBA Conversion = | 88% |

EXAMPLES 2–4

Using the equipment and following the procedures of Example 1, a series of pentasil, ZSM-5 zeolites were treated with 1.1:1 molar methanol/t-butanol mix at a range of operating temperatures, from 120° to 160° C. Concentrations of MTBE, isobutylene, diisobutylene, dimethyl ether, methanol and t-butanol in the product effluents, under the specified conditions as determined by glc, are summarized in the accompanying Tables 2–4.

In Example 2, the ZSM-5 with a silica/alumina ratio of shows:

| At 120° C.: | |
|---|---|
| tBA Conversion = | 67% |
| MTBE Selectivity = | 76% |
| Isobutylene Selectivity = | 23% |
| At 160° C.: | |
| tBA Conversion = ca. | 86% |

In Example 3, the ZSM-5 with a silica/alumina ratio of 31, shows:

| At 120° C.: | |
|---|---|
| tBA Conversion = | 51% |
| MTBE Selectivity = | 63% |
| Isobutylene Selectivity = | 33% |
| At 160° C.: | |
| tBA Conversion = ca. | 82% |

In Example 4, the ZSM-5 with a silica/alumina ratio of 350–370, shows:

| At 120° C.: | |
|---|---|
| tBA Conversion = | 39% |
| MTBE Selectivity = | 43% |
| Isobutylene Selectivity = | 53% |
| At 160° C.: | |
| tBA Conversion = ca. | 84% |

EXAMPLE 5

This examples illustrates the production of ethyl t-butyl ether from t-butanol and ethanol using a pentasil-type zeolite.

Synthesis was conducted in a tubular reactor ($\frac{3}{8}$" i.d., 12" long) constructed of 316 stainless steel, operated upflow and mounted in a furnace, controllable to ±1.0° C. and fitted with pumps allowing flow control to <±1 cc/hr. The reactor was also fitted with a pressure regulating device and equipment for monitoring temperature, pressure and flow rate.

The reactor was charged at the beginning of the experiment with 25 cc of ZSM-5 zeolite having a silica/alumina ratio of 140, with 20% alumina binder, as 1/16" diameter extrudates. A glass wool screen was placed at the top and bottom of the reactor to ensure the catalyst would remain in the middle portion.

The catalyst bed was treated with ethanol/t-butanol (1.1:1 molar mix) upflow, at a rate of 50 cc/hr, while the reactor was held at 120° C., with a total pressure of 300 psi. Samples of crude product effluent were collected periodically on stream, in 316 ss bombs and analyzed by glc.

Typical analyses data for samples taken under these conditions are summarized in Table 5. Concentrations of ETBE, isobutylene, diisobutylene, alkyl ether, ethanol and t-butanol in the reaction effluent were also measured at a series of higher temperatures (140°–160° C.). These data are also included in Table 5.

| For Sample #2, at 120° C.: | |
|---|---|
| tBA Conversion = | 59% |
| ETBE Selectivity = | 68% |
| Isobutylene Selectivity = | 24% |
| For Sample #5, at 160° C.: | |
| tBA Conversion = | 84% |

EXAMPLE 6

Using the equipment and following the procedures of Example 1, a sample of ZSM-5 zeolite catalyst (80% zeolite, 20% alumina) was treated with a crude 1.5:1 molar mix of ethanol and t-butanol feedstock that also contains significant quantities of water, isopropanol (2-PrOH), acetone ($Ac_2O$), and methyl ethyl ketone (MEK) Etherification was conducted at 120° C., 300 psi using a LHSV of 2.

Concentrations of each of these components, plus isobutylene, diisobutylene, diethyl ether (DEE) and ETBE, in the product effluents were determined by glc. Typical data are given in the accompanying Table 6. Over the period of the experiment, there were only modest changes in catalyst activity, as measured by the level of t-butanol conversion. Typical calculated conversion data are as follows:

| | Sample | | | |
|---|---|---|---|---|
| | 1 | 2 | 3 | 4 |
| Time on Stream (Days): | 1 | 11 | 17 | 23 |
| t-Butanol Conversion (%): | 50 | 49 | 47 | 43 |

TABLE 1

| | | | | | MTBE SYNTHESIS | | | | | | | |
|---|---|---|---|---|---|---|---|---|---|---|---|---|
| | | MeOH/tBA | Feed | | Time On | | PRODUCT COMPOSITION (Wt %) | | | | | |
| | | Molar | Rate | Temp. | Stream | | METHOD 26 | | | | METHOD 27 | |
| Ex. | Catalyst | Ratio | (cc/hr) | (°C.) | (Days) | SAMPLE | $H_2O$ | MeOH | $C_4H_8$ | tBA | MTBE | $C_8H_{16}$ | DME |
| 1 | 4179-CT90[a] | 1.1:1 | 50 | | | FS-1 | | 32.1 | | 67.6 | | | |
| | | | | 120 | 1 | →1 | 9.8 | 17.6 | 8.3 | 21.5 | 41.1 | — | 0.09 |
| | | | | | | 2 | 10.2 | 17.8 | 8.3 | 22.0 | 41.3 | — | 0.09 |
| | | | | 140 | 2 | 3 | 10.3 | 18.1 | 13.4 | 17.6 | 40.2 | 0.1 | 0.45 |
| | | | | | | 4 | 10.8 | 18.6 | 12.7 | 18.8 | 38.8 | 0.1 | 0.42 |
| | | | | 160 | 3 | →5[c] | 3.7 | 12.7 | 48.9 | 7.8 | 26.5 | 0.1 | 0.37 |
| | | | | | | | 32.5 | 42.2 | 4.4 | 9.8 | 10.4 | — | 0.41 |
| | | | | | | 6[d] | [b] | | | | | 0.1 | 0.36 |
| | | | | | | | 31.0 | 44.1 | 4.4 | 10.1 | 10.1 | — | 0.40 |

[a]80% ZSM-5, 20% $Al_2O_3$, 1/16"E, $SiO_2/Al_2O_3$: 140
[b]Analysis not available
[c]Relative phase sizes 3.67:1 (t:b)
[d]Relative phase sizes 3.56:1 (t:b)

TABLE 2

| | | | | | MTBE SYNTHESIS | | | | | | | |
|---|---|---|---|---|---|---|---|---|---|---|---|---|
| | | MeOH/tBA | Feed | | Time On | | PRODUCT COMPOSITION (Wt %) | | | | | |
| | | Molar | Rate | Temp. | Stream | | METHOD 26 | | | | METHOD 27 | |
| Ex. | Catalyst | Ratio | (cc/hr) | (°C.) | (Days) | SAMPLE | $H_2O$ | MeOH | $C_4H_8$ | tBA | MTBE | $C_8H_{16}$ | DME |
| 2 | 3038-CT90[a] | 1.1:1 | 50 | | | FS-1 | | 31.3 | | 67.9 | | | |
| | | | | 120 | 1 | →1 | 10.0 | 17.8 | 8.0 | 22.2 | 41.5 | — | 0.16 |
| | | | | | | 2 | 10.8 | 17.8 | 7.7 | 22.6 | 40.7 | — | 0.16 |
| | | | | 140 | 2 | 3 | 11.2 | 18.5 | 12.3 | 19.6 | 37.7 | 0.1 | 0.75 |
| | | | | | | 4 | 10.4 | 18.4 | 12.4 | 18.8 | 39.5 | 0.1 | 0.71 |
| | | | | 160 | 3 | →5[c] | 5.6 | 16.0 | 39.7 | 9.4 | 28.9[b] | — | 1.2[b] |
| | | | | | | | | | | | [c] | — | 1.0 |
| | | | | | | 6[d] | 4.3 | 14.7 | 41.8 | 8.8 | 29.9 | — | 1.0 |
| | | | | | | | 36.7 | 40.4 | 4.2 | 9.5 | 8.7 | — | 1.1 |

[a]80% ZSM-5, 20% $Al_2O_3$, 1/16"E, $SiO_2/Al_2O_3$: 51
[b]Similar data for repeat analysis
[c]Analysis not available

TABLE 3

| | | | | | MTBE SYNTHESIS | | | | | | | |
|---|---|---|---|---|---|---|---|---|---|---|---|---|
| | | MeOH/tBA | Feed | | Time On | | PRODUCT COMPOSITION (Wt %) | | | | | |
| | | Molar | Rate | Temp. | Stream | | METHOD 26 | | | | METHOD 27 | |
| Ex. | Catalyst | Ratio | (cc/hr) | (°C.) | (Days) | SAMPLE | $H_2O$ | MeOH | $C_4H_8$ | tBA | MTBE | $C_8H_{16}$ | DME |
| 3 | 4178-CT90[a] | 1.1:1 | 50 | | | FS-1 | | 30.9 | | 68.6 | | | |
| | | | | 120 | 1 | →1 | 7.4 | 23.4 | 8.8 | 33.6 | 26.3 | 0.1 | 0.16 |
| | | | | | | 2 | 7.5 | 23.4 | 8.3 | 35.4 | 24.7 | | 0.15 |
| | | | | 140 | 2 | 3 | 10.1 | 19.1 | 13.1 | 20.2 | 36.5 | | 0.46 |
| | | | | | | 4 | 10.3 | 19.5 | 12.3 | 20.8 | 36.6 | 0.1 | 0.44 |

TABLE 3-continued

| | | | | MTBE SYNTHESIS | | | | | | | | |
|---|---|---|---|---|---|---|---|---|---|---|---|---|
| | | | | Time | | | PRODUCT COMPOSITION (Wt %) | | | | | |
| | | MeOH/tBA | Feed | On | | | | METHOD 26 | | | METHOD 27 | |
| | | Molar | Rate | Temp. | Stream | | | | | | | |
| Ex. | Catalyst | Ratio | (cc/hr) | (°C.) | (Days) | SAMPLE | H₂O | MeOH | C₄H₈ | tBA | MTBE | C₈H₁₆ | DME |
| | | | | 160 | 3 | →5ᶜ | ᵇ | | | | | | |
| | | | | | | | 29.8 | 40.5 | 6.5 | 12.3 | 10.4 | — | 0.91 |
| | | | | | | 6ᵈ | ᵇ | | | | | | |
| | | | | | | | 29.7 | 40.2 | 6.3 | 13.3 | 10.0 | — | 0.88 |

ᵃ80% ZSM-5, 20% Al₂O₃, 1/16"E, SiO₂/Al₂O₃: 31
ᵇInsufficient quantity for analysis

TABLE 4

| | | | | MTBE SYNTHESIS | | | | | | | | |
|---|---|---|---|---|---|---|---|---|---|---|---|---|
| | | | | Time | | | PRODUCT COMPOSITION (Wt %) | | | | | |
| | | MeOH/tBA | Feed | On | | | | METHOD 26 | | | METHOD 27 | |
| | | Molar | Rate | Temp. | Stream | | | | | | | |
| Ex. | Catalyst | Ratio | (cc/hr) | (°C.) | (Days) | SAMPLE | H₂O | MeOH | C₄H₈ | tBA | MTBE | C₈H₁₆ | DME |
| 4 | 4034CT90ᵃ | 1.1:1 | 50 | | | FS-1 | | 31.2 | | 68.4 | | | |
| | | | | 120 | 1 | →1 | 5.5 | 27.6 | 10.7 | 41.9 | 13.4 | — | 0.24 |
| | | | | | | 2 | 5.3 | 28.0 | 10.9 | 46.2 | 9.2 | — | 0.24 |
| | | | | 140 | 2 | 3 | 9.9 | 22.1 | 14.7 | 24.6 | 28.1 | — | 0.34 |
| | | | | | | 4 | 9.5 | 22.0 | 15.2 | 24.4 | 28.3 | 0.1 | 0.30 |
| | | | | 160 | 3 | →5ᵇ | 5.3 | 16.1 | 41.3 | 10.7 | 25.8 | — | 0.32 |
| | | | | | | | 30.1 | 40.2 | 5.6 | 11.5 | 11.1 | 0.1 | 0.35 |
| | | | | | | 6ᶜ | 5.6 | 16.9 | 40.2 | 11.2 | 25.8 | — | 0.30 |
| | | | | | | | 29.8 | 40.7 | 5.9 | 12.4 | 10.7 | — | 0.33 |

ᵃ80% ZSM-5, S-115 from UOP, 1/16"E, SiO₂/Al₂O₃: 350–370
ᵇRelative phase sizes 4.40:1 (t:b)
ᶜRelative phase sizes 4.40:1 (t:b)

TABLE 5

| | | | | ETBE SYNTHESIS | | | | | | | | |
|---|---|---|---|---|---|---|---|---|---|---|---|---|
| | | | | Time | | | PRODUCT COMPOSITION (Wt %) | | | | | |
| | | EtOH/tBA | Feed | On | | | | METHOD 26 | | | METHOD 32 | |
| | | Molar | Rate | Temp. | Stream | | | | | | | |
| Ex. | Catalyst | Ratio | (cc/hr) | (°C.) | (Days) | SAMPLE | H₂O | EtOH | C₄H₈ | tBA | ETBE | C₈H₁₆ | DEE |
| 5 | 4179-CT-90ᵃ | 1.1:1 | 50 | | | FS-1 | | 42.5 | | 57.2 | | | |
| | | | | 120 | 1 | 1 | 6.9 | 28.3 | 12.8 | 25.1 | 26.3 | 0.3 | 0.10 |
| | | | | | | →2 | 6.5 | 27.0 | 14.2 | 23.7 | 28.2 | — | 0.10 |
| | | | | 140 | 2 | 3 | 7.6 | 26.9 | 17.9 | 19.3 | 27.5 | 0.3 | 0.31 |
| | | | | | | 4 | 7.9 | 27.6 | 17.7 | 19.3 | 27.0 | 0.1 | 0.29 |
| | | | | 160 | 3 | →5 | 9.8 | 31.4 | 34.3 | 9.2 | 14.4 | 0.1 | 0.59 |
| | | | | | | 6 | 10.2 | 31.7 | 32.3 | 10.1 | 14.5 | 0.2 | 0.54 |

ᵃ80% ZSM-5, 20% Al₂O₃, 1/16"E, SiO₂/Al₂O₃: 140

TABLE 6

| | | | Time | | | | | | | | | | | |
|---|---|---|---|---|---|---|---|---|---|---|---|---|---|---|
| | | Feed | On | | | PRODUCT COMPOSITION (Wt %) | | | | | | | | |
| | | Rate | Temp. | Stream | Sam- | | | METHOD 26 | | | | METHOD 32 | | |
| Ex. | Catalyst | (cc/hr) | (°C.) | (Days) | ple | H₂O | EtOH | C₄H₈ | MEK | tBA | ETBE | Ac₂O | 2-PrOH | C₈H₁₆ | DEE |
| 6 | 4179-CT-90ᵃ | 50ᵇ | | | FS-1 | 4.6 | 42.6 | | 1.5 | 45.8 | | 0.3 | 5.2 | | |
| | | | 120 | 1 | 1 | 8.5 | 32.8 | 9.1 | 1.5 | 22.8 | 20.3 | 0.3 | 5.2 | | 0.1 |
| | | | 11 | 2 | 2 | 8.3 | 33.3 | 9.3 | 1.6 | 23.5 | 18.7 | 0.6 | 5.2 | | |
| | | | | | FS-2 | 4.7 | 42.3 | | 1.5 | 45.7 | | 0.3 | 5.2 | | |
| | | | 17 | 3 | 3 | 8.2 | 33.7 | 9.8 | 1.6 | 24.0 | 17.5 | 0.3 | 5.4 | | |
| | | | | | FS-3 | 4.6 | 42.4 | | 1.5 | 45.6 | | 0.4 | 5.2 | | |
| | | | 23 | 4 | 4 | 8.0 | 35.0 | 9.3 | 1.6 | 25.9 | 15.1 | 0.3 | 5.3 | | |

ᵃ80% ZSM-5, 20% Al₂O₃, 1/16"E, SiO₂/Al₂O₃: 140
ᵇA EtOH:tBA (1.5:1) feedstock

What is claim is:

1. A method for synthesizing alkyl tertiary-butyl ethers which comprises reacting a $C_4$–$C_{10}$ tertiary alcohol with a $C_1$–$C_6$ primary alcohol in the presence of a catalyst comprising a pentasil zeolite having a silica/alumina ratio of 50:1 to 150:1 optionally in the presence of a binder consisting essentially of an oxide of an element selected from Group III or IV of the Periodic Table and continuously contacting said primary alcohol and tertiary alcohol in a molar amount of from about 10:1 to 1:10 over said pentasil zeolite catalyst at a temperature of about 80° C. to about 200° C. and a pressure of about atmospheric to about 1000 psig to obtain alkyl tert-alkyl ether product.

2. The method of claim 1 wherein the tertiary alcohol is tert-butanol, the primary alcohol is methanol and the alkyl tertiary-butyl ether is methyl tertiary butyl ether (MTBE).

3. The method of claim 1 wherein the tertiary alcohol is tert-butanol, the primary alcohol is ethanol and the alkyl tertiary alkyl ether is ethyl tertiary butyl ether (ETBE).

4. The method of claim 1 wherein the pentasil zeolite has a silica:alumina ratio of 120 to 150.

5. The method of claim 1 wherein the pentasil zeolite catalyst is bound to a Group III or Group IV oxide.

6. The method of claim 5 wherein the Group III oxide binder is alumina.

7. The method of claim 6 wherein the alumina comprises 1% to 40% of the formed catalyst.

8. The method of claim 2 wherein the operating temperature is in the range of about 140° C. to 200° C. and the product comprises a two-phase mix of an MTBE-isobutylene product rich phase and a heavier aqueous methanol-rich phase.

* * * * *